(12) United States Patent
Villegas

(10) Patent No.: US 8,255,025 B2
(45) Date of Patent: Aug. 28, 2012

(54) BRONCHIAL OR TRACHEAL TISSULAR WATER CONTENT SENSOR AND SYSTEM

(75) Inventor: Diana Villegas, Alameda, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1494 days.

(21) Appl. No.: 11/449,928

(22) Filed: Jun. 9, 2006

(65) Prior Publication Data

US 2007/0299357 A1    Dec. 27, 2007

(51) Int. Cl.
*A61B 5/00* (2006.01)
(52) U.S. Cl. ........ 600/310; 600/476; 600/473; 600/478; 600/529
(58) Field of Classification Search .......... 600/473, 600/476, 310, 529, 478
See application file for complete search history.

(56) References Cited

U.S. PATENT DOCUMENTS

| | | |
|---|---|---|
| 3,998,550 A | 12/1976 | Konishi et al. |
| 4,066,068 A | 1/1978 | Nilsson et al. |
| 4,364,008 A | 12/1982 | Jacques |
| 4,711,244 A | 12/1987 | Kuzara |
| 4,723,554 A | 2/1988 | Oman et al. |
| 4,805,365 A | 2/1989 | Bastian |
| 4,850,365 A | 7/1989 | Rosenthal |
| 4,860,753 A | 8/1989 | Amerena |
| 4,883,055 A | 11/1989 | Merrick |
| 4,907,594 A | 3/1990 | Muz |
| 5,057,695 A | 10/1991 | Hirao et al. |
| 5,086,781 A | 2/1992 | Bookspan |
| 5,111,817 A | 5/1992 | Clark et al. |
| 5,146,091 A | 9/1992 | Knudson |
| 5,224,478 A | 7/1993 | Sakai et al. |
| 5,277,181 A | 1/1994 | Mendelson et al. |
| 5,279,295 A | 1/1994 | Martens et al. |
| 5,282,467 A | 2/1994 | Piantadosi et al. |
| 5,337,745 A | 8/1994 | Benaron |
| 5,337,937 A | 8/1994 | Remiszewski et al. |

(Continued)

FOREIGN PATENT DOCUMENTS

EP    1184663    3/2002

(Continued)

OTHER PUBLICATIONS

Grandjean et al., "Hydration: Issues for the 21$^{st}$ Century"; *Nutrition Reviews*, vol. 61, No. 8, pp. 261-271.

(Continued)

*Primary Examiner* — Brian Casler
*Assistant Examiner* — Amanda Lauritzen
(74) *Attorney, Agent, or Firm* — Fletcher Yoder

(57) ABSTRACT

The disclosure provides a sensor system for detecting bronchial tissular water content including at least a sensor, a connector, and a monitor. The sensor generates a signal, which may be carried by the connector to the monitor, which generates an output corresponding to the signal. The disclosure additionally provides a sensor for detecting bronchial or tracheal tissular water content including at least a signal generator. The sensor may also include at least a segment of a connector. The disclosure also provides a method of measuring bronchial or tracheal tissular water content by inserting a sensor into an airway of a subject, such as a human, until it becomes lodged in a bronchus or the trachea, then measuring bronchial or tracheal tissular water content using the sensor.

36 Claims, 2 Drawing Sheets

U.S. PATENT DOCUMENTS

| | | | |
|---|---|---|---|
| 5,348,004 A | 9/1994 | Hollub | |
| 5,355,880 A | 10/1994 | Thomas et al. | |
| 5,368,027 A | 11/1994 | Lubbers et al. | |
| 5,368,224 A | 11/1994 | Richardson et al. | |
| 5,377,674 A | 1/1995 | Kuestner | |
| 5,499,627 A | 3/1996 | Steuer et al. | |
| 5,546,935 A | 8/1996 | Champeau | |
| 5,555,882 A | 9/1996 | Richardson et al. | |
| 5,615,689 A | 4/1997 | Kotler | |
| 5,660,567 A | 8/1997 | Neirlich et al. | |
| 5,687,721 A | 11/1997 | Kuhls | |
| 5,701,902 A | 12/1997 | Vari et al. | |
| 5,713,355 A | 2/1998 | Richardson et al. | |
| 5,720,284 A | 2/1998 | Aoyagi et al. | |
| 5,735,284 A | 4/1998 | Tsoglin et al. | |
| 5,747,789 A | 5/1998 | Godik | |
| 5,755,672 A | 5/1998 | Arai et al. | |
| 5,788,643 A | 8/1998 | Feldman | |
| 5,803,908 A | 9/1998 | Steuer et al. | |
| 5,827,181 A | 10/1998 | Dias et al. | |
| 5,830,136 A | 11/1998 | Delonzor et al. | |
| 5,833,602 A | 11/1998 | Osemwota | |
| 5,853,364 A | 12/1998 | Baker, Jr. et al. | |
| 5,860,919 A | 1/1999 | Kiani et al. | |
| 5,885,213 A | 3/1999 | Richardson et al. | |
| 5,906,582 A | 5/1999 | Kondo et al. | |
| 6,044,283 A | 3/2000 | Fein et al. | |
| 6,064,898 A | 5/2000 | Aldrich | |
| 6,083,172 A | 7/2000 | Baker, Jr. et al. | |
| 6,125,297 A | 9/2000 | Siconolfi | |
| 6,149,591 A | 11/2000 | Henderson et al. | |
| 6,178,342 B1 | 1/2001 | Thompson et al. | |
| 6,222,189 B1 | 4/2001 | Misner et al. | |
| 6,246,894 B1 | 6/2001 | Steuer et al. | |
| 6,278,523 B1* | 8/2001 | Gorecki | 356/450 |
| 6,280,396 B1 | 8/2001 | Clark et al. | |
| 6,336,044 B1 | 1/2002 | Ghiassi et al. | |
| 6,370,426 B1 | 4/2002 | Campbell et al. | |
| 6,400,971 B1 | 6/2002 | Finarov et al. | |
| 6,402,690 B1 | 6/2002 | Rhee et al. | |
| 6,411,833 B1 | 6/2002 | Baker, Jr. et al. | |
| 6,442,408 B1 | 8/2002 | Wenzel et al. | |
| 6,466,807 B1 | 10/2002 | Dobson et al. | |
| 6,488,677 B1 | 12/2002 | Bowman et al. | |
| 6,512,936 B1 | 1/2003 | Monfre et al. | |
| 6,591,122 B2 | 7/2003 | Schmitt | |
| 6,592,574 B1 | 7/2003 | Shimmick et al. | |
| 6,600,946 B1 | 7/2003 | Rice | |
| 6,606,509 B2 | 8/2003 | Schmitt | |
| 6,615,064 B1 | 9/2003 | Aldrich | |
| 6,635,491 B1 | 10/2003 | Khalil et al. | |
| 6,636,759 B2 | 10/2003 | Robinson | |
| 6,643,543 B2 | 11/2003 | Takehara et al. | |
| 6,654,620 B2 | 11/2003 | Wu et al. | |
| 6,668,181 B2 | 12/2003 | Wenzel et al. | |
| 6,675,029 B2 | 1/2004 | Monfre et al. | |
| 6,687,519 B2 | 2/2004 | Steuer et al. | |
| 6,708,049 B1* | 3/2004 | Berson et al. | 600/323 |
| 6,721,584 B2 | 4/2004 | Baker, Jr. et al. | |
| 6,777,240 B2 | 8/2004 | Hazen et al. | |
| 6,819,687 B1 | 11/2004 | Fein | |
| 6,836,679 B2 | 12/2004 | Baker, Jr. et al. | |
| 6,849,046 B1 | 2/2005 | Eyal-Bickels | |
| 6,873,865 B2 | 3/2005 | Steuer et al. | |
| 6,882,874 B2 | 4/2005 | Huiku | |
| 6,950,699 B1 | 9/2005 | Manwaring et al. | |
| 6,961,598 B2 | 11/2005 | Diab | |
| 7,215,991 B2 | 5/2007 | Besson et al. | |
| 7,236,811 B2 | 6/2007 | Schmitt | |
| 7,239,902 B2 | 7/2007 | Schmitt et al. | |
| 7,277,741 B2 | 10/2007 | Debreczeny et al. | |
| 7,283,242 B2 | 10/2007 | Thornton | |
| 7,343,186 B2 | 3/2008 | Lamego et al. | |
| 7,657,292 B2* | 2/2010 | Baker et al. | 600/310 |
| 8,135,448 B2* | 3/2012 | Baker et al. | 600/310 |
| 2001/0020122 A1 | 9/2001 | Steuer et al. | |
| 2002/0169388 A1 | 11/2002 | Bowman et al. | |
| 2003/0060693 A1 | 3/2003 | Monfre et al. | |
| 2004/0127777 A1 | 7/2004 | Richti et al. | |
| 2004/0147034 A1 | 7/2004 | Gore et al. | |
| 2004/0230106 A1* | 11/2004 | Schmitt et al. | 600/310 |
| 2005/0119538 A1 | 6/2005 | Jeon et al. | |
| 2005/0267346 A1 | 12/2005 | Faber et al. | |
| 2006/0020181 A1 | 1/2006 | Schmitt | |
| 2006/0052661 A1* | 3/2006 | Gannot et al. | 600/108 |
| 2006/0052680 A1 | 3/2006 | Diab | |
| 2006/0084864 A1 | 4/2006 | Schmitt et al. | |
| 2006/0167350 A1 | 7/2006 | Monfre et al. | |
| 2006/0224053 A1 | 10/2006 | Black et al. | |
| 2006/0235348 A1* | 10/2006 | Callicoat et al. | 604/4.01 |
| 2006/0253007 A1 | 11/2006 | Cheng et al. | |
| 2006/0253016 A1* | 11/2006 | Baker et al. | 600/410 |
| 2006/0276696 A1 | 12/2006 | Schurman | |
| 2007/0078311 A1 | 4/2007 | Al-Ali et al. | |
| 2007/0093702 A1 | 4/2007 | Yu et al. | |
| 2007/0106137 A1 | 5/2007 | Baker, Jr. et al. | |
| 2007/0118027 A1 | 5/2007 | Baker, Jr. et al. | |
| 2007/0129614 A1 | 6/2007 | Schmitt et al. | |
| 2007/0167693 A1 | 7/2007 | Scholler et al. | |
| 2007/0282178 A1 | 12/2007 | Scholler et al. | |
| 2007/0282183 A1 | 12/2007 | Scholler et al. | |
| 2008/0004513 A1 | 1/2008 | Walker et al. | |
| 2008/0009690 A1 | 1/2008 | Debreczeny et al. | |
| 2008/0076983 A1 | 3/2008 | Debreczeny et al. | |
| 2008/0077023 A1 | 3/2008 | Campbell et al. | |
| 2008/0081975 A1 | 4/2008 | Agashe et al. | |
| 2008/0097173 A1 | 4/2008 | Soyemi et al. | |
| 2008/0146906 A1 | 6/2008 | Baker, Jr. et al. | |
| 2008/0154104 A1 | 6/2008 | Lamego et al. | |
| 2008/0220512 A1 | 9/2008 | Koh et al. | |
| 2008/0221406 A1 | 9/2008 | Baker, Jr. | |
| 2008/0221407 A1 | 9/2008 | Baker, Jr. | |
| 2008/0221409 A1 | 9/2008 | Hoarau | |
| 2008/0221410 A1 | 9/2008 | Campbell et al. | |
| 2008/0221411 A1 | 9/2008 | Hausmann et al. | |
| 2008/0221412 A1 | 9/2008 | Baker, Jr. et al. | |
| 2008/0221414 A1 | 9/2008 | Baker, Jr. | |
| 2008/0221416 A1 | 9/2008 | Baker, Jr. | |
| 2009/0216096 A1 | 8/2009 | Bloom et al. | |

FOREIGN PATENT DOCUMENTS

| | | |
|---|---|---|
| EP | 1 238 630 A | 9/2002 |
| FR | 2710517 | 4/1995 |
| JP | 11244266 | 9/1999 |
| JP | 2004081427 | 3/2004 |
| JP | 25169020 | 6/2005 |
| JP | 25278758 | 10/2005 |
| JP | 26075354 | 3/2006 |
| WO | WO 88/06860 A | 9/1988 |
| WO | WO9313706 | 7/1993 |
| WO | WO9519562 | 7/1995 |
| WO | WO9834097 | 8/1998 |
| WO | WO 99/03393 A | 1/1999 |
| WO | WO0071025 | 11/2000 |
| WO | WO0116577 | 3/2001 |
| WO | WO03010510 | 2/2003 |
| WO | WO2005041765 | 5/2005 |
| WO | WO 2006/015230 A | 2/2006 |

OTHER PUBLICATIONS

Arimoto et al., "Non-contact Skin Moisture Measurement Based on Near-Infrared Spectroscopy," *Applied Spectroscopy*, vol. 58, No. 12, pp. 1439-1446.

Buijs, K., et al., "Near-Infrared Studies of the Structure of Water. I. Pure Water," *The Journal of Chemical Physics*, vol. 39, No. 8, pp. 2035-2041 (Oct. 15, 1963).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Bommannan, D., et al., "Examination of Stratum Corneum Barrier Function In Vivo by Infrared Spectroscopy," *J. Invest Dermatol*, vol. 95, pp. 403-408 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Martin, K., "Direct Measurement of Moisture in Skin by NIR spectroscopy," *J. Soc. Cosmet. Chem.*, 44:249-261 (1993).

Matcher, S. J., et al., "Absolute quantification of deoxyhaemoglobin concentration in tissue near infrared spectroscopy," *Phys. Med. Biol.*, vol. 39, pp. 1295-1312 (1994).

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Schmitt et al., *Proc. SPIE*, "Optimum wavelengths for measurement of blood hemoglobin content and tissue hydration by NIR spectrophotometry," 2678:442-453 (1996).

Martin, Kathleen, "In Vivo Measurements of Water in Skin by Near-Infrared Reflectance," *Applied Spectroscopy*, vol. 52, No. 7, 1998, pp. 1001-1007.

Stranc, M.F., et al., "Assessment of tissue viability using near-infrared spectroscopy," *British Journal of Plastic Surgery*, vol. 51, pp. 210-217, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Fornetti, Willa C., et al., "Reliability and validity of body composition measures in female athletes," Journal of Applied Physiology, vol. 87, pp. 1114-1122, (1999).

Lucassen, G., et al., "Water Content and Water Profiles in Skin Measured by FTIR and Raman Spectroscopy," *Proc. SPIE*, vol. 4162, pp. 39-45 (2000).

Attas, Michael, et al., "Visualization of cutaneous hemoglobin oxygenation and skin hydration using near-infrared spectroscopic imaging," *Skin Research and Technology*, vol. 7, pp. 238-245, (2001).

Du, Y., et al., "Optical properties of porcine skin dermis between 900 nm and 1500 nm," *Phys. Med. Biol.*, vol. 46, pp. 167-181 (2001).

Lever, M., et al., "Some ways of looking at compensatory kosmotropes and different water environments," *Comparative Biochemistry and Physiolog.*, vol. 130, Part A, pp. 471-486, (2001).

Sowa et al., "Near infrared spectroscopic assessment of hemodynamic changes in the early post-burn period," *Burns*, 27(3):241-9 (2001).

Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (Feb. 28, 2002), vol. 28, No. 1, p. 37-43.

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Bouwstra, Joke A., et al., "Water Distribution and Related Morphology in Human Stratum Corneum at Different Hydratin Levels," *J. Invest Dermatol*, vol. 150, pp. 750-758 (2003).

Grandjean et al., "Hydration: issues for the $21^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp. 1471-1477 (2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, pp. 185-190 (Apr. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

Arimoto et al., "Non-contact skin moisture measurement based on near-infrared spectroscopy", *Applied Spectroscopy*, 58(12):1439-1445 (2004).

Yamakoshi, K.. et al.; "Electrical admittance cuff for non-invasive and simultaneous measurement of hematocrit, arterial pressure and elasticity using volume-oscillometric method," *Med. & Biol. Eng. & Comput.*,; pp. S99-S107; Jul. 1994.

Yamakoshi, K. et al.; "Noninvasive Measurement of Hematocrit by Electrical Admittance Plethysmography Technique," *IEEE Transactions on Biomedical Engineering*, vol. BME-27, No. 3; pp. 156-161; Mar. 1980.

Grandjean et al., "Hydration: Issues for the 21st Century"; Nutrition Reviews, vol. 61, No. 8, pp. 261-271.

Arimoto et al., "Non-contact Skin Moisture Measurement Based on Near-Infrared Spectroscopy," Applied Spectroscopy, Volumn 58, No. 12, pp. 1439-1446.

Kathleen Martin, "In Vivo Measurements of Water in Skin by Near-Infrared Reflectance," Applied Spectroscopy, vol. 52, No. 7, pp. 1001-1007.

Sowa et al., "Near Infrared Spectroscopic Assessment of Tissue Hydration Following Surgery," Journal of Surgical Research, vol. 86, pp. 62-69.

* cited by examiner

BRONCHIAL OR TRACHEAL TISSULAR WATER CONTENT SENSOR AND SYSTEM

TECHNICAL FIELD

The present disclosure is related to a tissular water content sensor and/or system, e.g. a lung or bronchial or tracheal tissular water content sensor and/or system.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Water content in the lungs is critical to human life. Proper pulmonary circulation of blood is very important in maintaining adequate gas exchange. The pulmonary vessels arrive from the right ventricle and divide into branches forming thin sheets of capillary network in the alveolar wall. Gas exchange occurs by diffusion between these thin capillaries and alveolar membranes. Continuous transudation of fluid in the alveolar interstitial space from the alveolar capillaries and extra-alveolar arterioles occurs normally. The fluid supplies nutrients to the lung tissue and is reabsorbed at the venular end of the capillaries or by lymphatic system.

Excess amounts of fluid may accumulate in the alveolar or lung tissue and interfere with gas exchange. Accumulation of excess water is referred to as alveolar or pulmonary edema. The four major pathophysiologic mechanisms for development of alveolar edema are: 1)increased hydrostatic pressure e.g. left heart failure 2)decreased oncotic pressure e.g. overhydration, nephrosis 3)increased capillary permeability e.g. infection, exposure to toxic substances and 4)obstruction of the lymphatic system.

Alveolar or pulmonary edema often manifests as difficulty in breathing, diaphoresis and cough. On examination patients may appear anxious, with presence of tachycardia, cyanosis, pulmonary rales, rhonchi and/or wheeze and arterial hypoxemia. The pulmonary capillary wedge pressure may be elevated and chest x-ray may show vascular redistribution, blurriness of vascular outlines, increased interstitial markings and/or butterfly pattern characteristic of alveolar edema. The clinical presentation may not be clear especially in unconscious patients. In some clinical situations such as sepsis, lung injury or pneumonia the clinical presentation may overlap. The pulmonary capillary wedge pressure used for diagnosis and monitoring of pulmonary edema is an invasive procedure and may not be an effective diagnostic and monitoring tool in some situations where the pulmonary edema is secondary to non-cardiac etiologies.

SUMMARY

A summary of certain exemplary embodiments is set forth below. It should be understood that this summary is presented merely to provide the reader with a brief description of certain forms the invention might take and that these aspects are not intended to limit the scope of the invention. Indeed, the invention may encompass a variety of aspects that may not be set forth below.

According to one embodiment of the present disclosure, a sensor system may be provided. The sensor system may include a bronchial or tracheal tissular water sensor operable to generate a signal corresponding to bronchial or tracheal tissular water when placed adjacent to a bronchial or tracheal tissue. It may also include a connector operable to carry the signal and a monitor operable to receive the signal and generate an output corresponding to the signal.

According to another embodiment of the present disclosure, another sensor system may be provided. The sensor system may include means for sensing bronchial or tracheal tissular water when placed adjacent to a bronchial or tracheal tissue and means for generating a signal corresponding to bronchial or tracheal tissular water. It may also include means for carrying the signal and means for receiving the signal and generating an output corresponding to the signal.

According to yet another embodiment of the present disclosure, a sensor may be provided. The sensor may include a signal generator operable to sense bronchial or tracheal tissular water and generate a signal corresponding to bronchial or tracheal tissular water when placed adjacent to a bronchial or tracheal tissue.

In a more specific embodiment, the sensor may also include at least a segment of a connector coupled to the signal generator and operable to carry the signal.

In another embodiment, the disclosure describes a sensor that may include a signal generation device operable to sense bronchial or tracheal tissular water and generate a signal corresponding to bronchial or tracheal tissular water when placed adjacent to a bronchial or tracheal tissue.

In a more specific embodiment, the sensor may include at least a portion of a connector coupled to the signal generator and operable to carry the signal.

Another embodiment of the disclosure relates to a method of measuring bronchial or tracheal tissular water content in a subject. The method may include inserting a sensor and at least a portion of a connector into an airway of the subject, lodging the sensor in a bronchus or the trachea such that at least a portion of the sensor is adjacent to a bronchial or tracheal wall, generating a signal corresponding to tissular water content using the sensor, conveying the signal from the sensor to the connector, conveying the signal from the connector to a monitor, and providing information corresponding to tissular water content using the signal and the monitor.

In a more specific embodiment, the method may include connecting a replaceable sensor component to a sensor system prior to inserting the sensor.

In an even more specific embodiment, the method may include removing the sensor from the subject after providing information and disconnecting the replaceable sensor component from the sensor system.

BRIEF DESCRIPTION OF THE DRAWINGS

A more complete and thorough understanding of the present embodiments may be acquired by referring to the following description taken in conjunction with the accompanying drawings, in which like reference numbers indicate like features.

Figure 1:
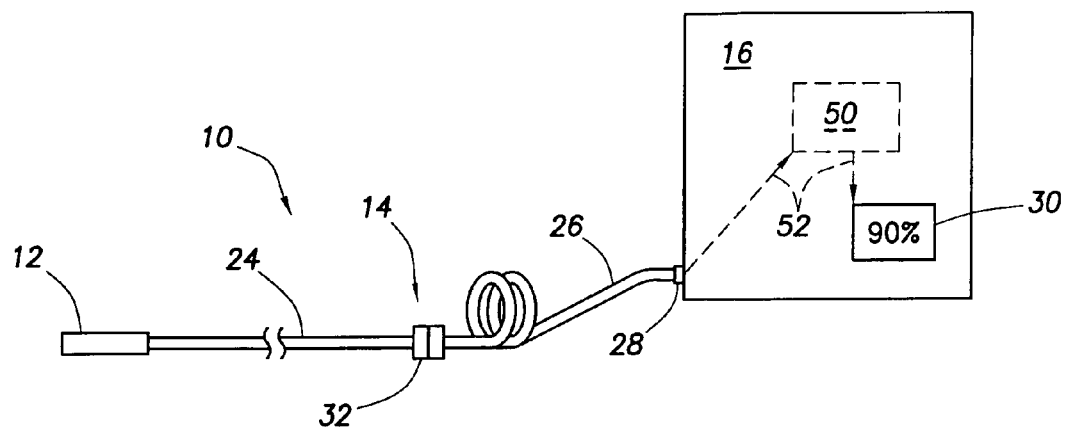
FIG. 1 is a diagram of a bronchial or tracheal sensor system, according to an embodiment of the present disclosure.

While the invention is susceptible to various modifications and alternative forms, specific embodiments have been shown by way of example in the drawings and will be described in detail herein. However, it should be understood that the invention is not intended to be limited to the particular forms enclosed. Rather, the invention is to cover all modifications, equivalents and alternatives falling within the spirit and scope of the invention as defined by the appended claims.

DETAILED DESCRIPTION

Early diagnosis and effective monitoring of alveolar edema by measurement of alveolar water content may provide clinicians with a tool to better manage their patients and improve the treatment outcome. Accordingly, the present disclosure is directed to a tissular water content sensor and/or system, e.g. a lung or bronchial or tracheal tissular water content sensor and/or system.

Selected embodiments of the disclosure are best understood by reference to FIGS. 1-6, wherein like numbers refer to the same or similar parts.

Referring now to the embodiment of FIG. 1, sensor system 10 may include tissular water sensor 12 attached to connector 14, which may include shaft 24, cable 26, and coupler 32. Connector 14 may be attached to monitor 16 via coupler 28. Monitor 16 may include display 30.

Sensor system 10 may be able to measure tissular water content in lung tissue, specifically bronchial or tracheal tissue, when placed adjacent to such tissue. Sensor system 10 may be able to sense tissular water content spectroscopically because absorbance of many tissues is related to water content. It may also function using Near Infrared Reflectance or Spectroscopy, such as variations of that described in Sowa, M. G. et al., *Near Infrared Spectroscopic Assessment of Tissue Hydration Following Surgery*, J. of Surgical Res.:86, 62-69 (1999) and Martin, K., In Vivo *Measurements of Water in Skin by Near-Infrared Reflectance*, Applied Spectroscopy: 52, 1001-07 (1998), both incorporated by reference herein. Laser Doppler measurements may be used in some embodiments.

Sensor 12 may include any type of sensor able to measure water content in adjacent bronchial or tracheal tissue. Specifically, it may include an optical sensor. It may also include a tissue hydration probe, for example, such as those described more fully in U.S. Pat. No. 6,591,122 and U.S. 2004/0230106, both incorporated by reference herein. One example of a tissue hydration probe provides a device for measuring a body-tissue water content metric as a fraction of the fat-free tissue content of a patient using optical spectrophotometry. The device includes a probe housing configured to be placed near a tissue location which is being monitored; light emission optics connected to the housing and configured to direct radiation at the tissue location; light detection optics connected to the housing and configured to receive radiation from the tissue location; and a processing device configured to process radiation from the light emission optics and the light detection optics to compute the metric where the metric includes a ratio of the water content of a portion of patient's tissue in relation to the lean or fat-free content of a portion of patient's tissue. Specifically, light emitting diodes (LEDs) emit light at selected wavelengths and a photodiode measures the transmitted light. Alternately, the photodiode can be placed adjacent to the LEDs to allow for the measurement of the reflectance of the emitted light. A preamplifier magnifies the detected signal for processing by a microprocessor. The microprocessor determines the tissue water fraction. Sensor 12 may measure tissular water content directly, or indirectly through, for example, a chemical detection system. Such a chemical detection system may include an indicator chemical whose characteristics may be altered by properties of the surrounding tissue, e.g., water content, extracellular water, or pH.

Sensor 12 may be small enough to pass through the upper respiratory tract, and into a bronchus, but large enough to contact a bronchial wall before reaching the alveoli. Sensor 12 may also be small enough to pass into the trachea, but large enough to contact a tracheal wall. Specifically, sensor 12 may be large enough to be in approximately full contact with at least a portion of the bronchial or tracheal wall. For example, sensor 12 may have an ellipsoid cross-sectional shape and may have an approximate diameter of at least approximately 1 mm, 2 mm, or 3 mm and at most approximately 4 mm, 5 mm or 6 mm.

Figure 4:
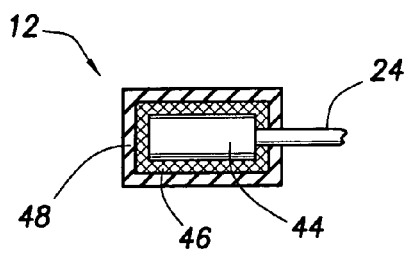
FIG. 4 is a diagram of a lengthwise section of a sensor in a bronchial or tracheal sensor system, according to an embodiment of the present disclosure.
Figure 6:
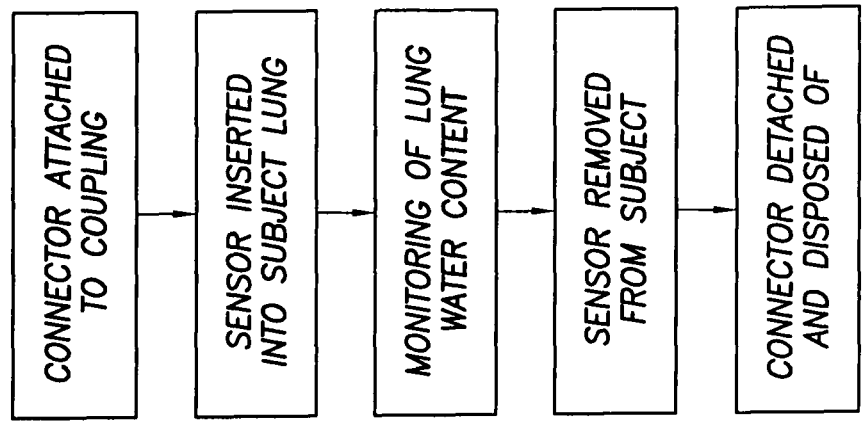
FIG. 6 is a block diagram of a process for using a bronchial or tracheal sensor system according to an embodiment of the present disclosure.

Sensor 12, shown in greater detail in FIG. 4, may contain signal generator 44, indicator 46 and outer portion 48. Signal generator 44 may include a sensor mechanism such as a microchip, but it may also include other components, such as a light gathering end of an optical fiber or an electrically conductive material. Signal generator 44 may generate a signal based on indicator 46. Indicator 46 may include, for example, a chemical indicator, e.g. a fluorescent molecule.

Indicator 46 may include one or multiple chemicals, e.g. fluorescent molecules and/or chemicals that react with fluorescent molecules, and may change characteristics based on properties of the bronchial or tracheal wall that indicate tissular water content. Outer portion 48 may be formed from any material exhibiting short-term or long-term biocompatibility. Specifically, it may be formed from any material known to be biocompatible for a given period of time, e.g., at least one week.

Outer portion 48 may also be selected to protect internal components, for example, from bodily fluids that might interfere with their function. However, outer portion 48 may also be selected to not unduly interfere with the function of indicator 46 and/or generation of a signal in signal generator 44.

In some embodiments, not explicitly shown, sensor 12 may omit indicator 46 and include only signal generator 44 and/or outer portion 48. In such embodiments, signal generator 44 may be able to generate a signal without any indicator.

Sensor 12 may be incorporated into an existing medical device, such as an endotracheal tube, an endobronchial tube, a bronchoscope, and other devices that may be introdueced into the tracheo-bronchial system to diagnose or treat respiratory or systemic conditions. In a further example, sensor 12 may be incorporated into the wall of such a tube.

Sensor 12 may contain a hollow region to allow airflow through it. Such a sensor may be sufficiently large to contact nearly the full diameter of the trachea or a bronchus.

Sensor 12 may be integrally formed with at least a portion of connector 14, or it may be coupled to connector 14 via a coupler, not explicitly shown. Such a coupler may be formed of two distinct parts, for example, one part attached to sensor 12 and one part attached to connector 14, that allow transmission of a signal from sensor 12 to connector 14 when brought adjacent to one another. The two parts may also be designed to remain in place when brought adjacent to one another. The two parts may also be designed to be releasable from one another. The coupler may allow conversion of a signal from one type to another, for example, from an optical signal to a digital or analog signal, and/or from a digital signal to an analog signal, or vice versa.

In some embodiments, sensor 12 may be provided separately from the rest of sensor system 10 to allow use of a different sensor for each subject, while the remainder of the system may be reused for multiple subjects. In these embodiments, the sensor and connector 14 may be connected via a coupler as described above rather than integrally formed. The coupler may be designed to allow easy replacement of the sensor. This may help mitigate sterilization and disease transmission concerns as well as concerns that the sensor may not function as well after having been used once.

Sensor 12 may be designed to provide signature data, thereby allowing authentication of accuracy, for example as described in U.S. Pat. No. 6,708,049, incorporated by reference herein.

Figure 2:
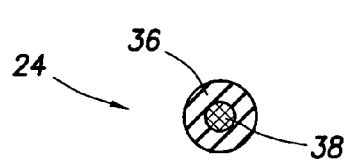
FIG. 2 is a diagram of a cross section of a shaft in a bronchial or tracheal sensor system, according to an embodiment of the present disclosure.
Figure 3:
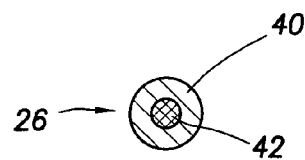
FIG. 3 is a diagram of a cross section of a cable in a bronchial or tracheal sensor system, according to an embodiment of the present disclosure.

Connector 14 as illustrated in the embodiment of FIG. 1 may include shaft 24 connected which may be to cable 26 via coupler 32. Shaft 24 may be rigid and/or semi-rigid. As shown in FIG. 2, shaft 24 may have outer portion 36 that may be formed from any material exhibiting short-term or long-term biocompatibility. Specifically, it may be formed from any material known to be biocompatible for a given period of time, e.g., at least one week. Outer portion 36 may also be selected to protect internal components, for example, from bodily fluids that might interfere with their function. Shaft 24 may also have inner portion 38 which may be able to carry the signal and may contain, for example, a component such as an optical fiber or an electrically conductive material operable to convey a signal from sensor 12 at least to coupler 32 so that the signal may ultimately reach monitor 16.

Shaft 24 may be approximately as long as is normally required to reach from the exterior of the mouth or nose, through the upper respiratory tract, and into the trachea or a bronchus in the lungs in an adult human. For example, shaft 24 may be at least approximately 2 feet long or at least approximately 3 feet long. Different lengths may be selected as appropriate for different subjects, such as shorter lengths for an infant or juvenile human or small animal and longer lengths for a large animal. Shaft 24 may be a medical device inserted in the patient for other purposes, e.g. an endotracheal tube or a tracheostomy tube.

Cable 26 may include outer portion 40 and inner portion 42. Inner portion 42 may include a component operable to transmit a signal at least from connector 32 to monitor 16. The component may, for example, include an optical fiber or an electrically conductive material. Outer portion 40 may include a protective material operable to protect a component in inner portion 42, for example, from the external environment. Outer portion 40 of cable 26 may not necessarily be biocompatible.

Cable 26 may be any length appropriate to situate monitor 16 a suitable distance away from any subject so as not to interfere with treatment or monitoring of the subject. For example, cable 26 might be at least approximately 2 feet long, approximately 3 feet long, or approximately 5 feet long. Different lengths may be selected as appropriate for different subjects, such as shorter lengths for an infant or juvenile human or small animal and longer lengths for a large animal.

A portion of shaft 24 and/or cable 24, particularly the inner portion thereof, may include an optical corner turner, for example such as that described in U.S. Pat. No. 6,819,687, incorporated by reference herein.

Coupler 32 may be operable to allow transmission of a signal from shaft 24 to cable 26. Coupler 32 may be formed of two distinct parts, for example one part attached to shaft 24 and one part attached to cable 26, that allow transmission of a signal from sensor 12 through connector 14 to monitor 16 when brought adjacent to one another. The two parts may also be designed to remain in place when brought adjacent to one another. The two parts may also be designed to be releasable from one another. Coupler 32 may allow conversion of a signal from one type to another, for example from an optical signal to a digital or analog signal, or from a digital signal to an analog signal, or vice versa.

Coupler 28 may be operable to allow transmission of a signal from connector 14 to monitor 16. Coupler 28 may be formed of two parts, for example one part attached to connector 14 and one part attached to monitor 16, that allow signal transmission when brought adjacent to one another. The two parts may also be designed to remain in place when brought adjacent to one another. The two parts may also be designed to be releasable from one another. Coupler 28 may allow conversion of a signal from one type to another, for example from an optical signal to a digital or analog signal, or from a digital signal to an analog signal, or vice versa.

One or more of the couplers that may be used in various embodiments of the disclosure may contain an encoding device, for example one such as the removable encoding device of U.S. Pat. No. 5,660,567, incorporated by reference herein.

Connector 14 need not be formed in all embodiments of two long segments and a connector as shown in the embodiment of FIG. 1. It may instead be formed of one integral segment, or from more than two long segments and multiple couplers as needed.

Further, in one embodiment, the disclosure may include a truncated segment of connector 14. Specifically, it may include sensor 12, shaft 24 and all or a portion of coupler 32. The truncated segment may be provided separately from the rest of sensor system 10 to allow use of a separate truncated segment for each subject, while the remainder of the system may be reused for multiple subjects. Alternatively, connector 14 may be designed to be replaceable in its entirely between subjects. Coupler 28 or coupler 32 may be designed to allow easy replacement of all or a truncated segment of connector 14, respectively, in these embodiments. Both embodiments help mitigate sterilization and disease transmission concerns that might arise of the same portion of connector 14 that is placed inside the subject were used for more than one subject.

Used replaceable parts, such as a replaceable sensor 12, replaceable segment of connector 14, or replaceable connector 14 may be reused. Such parts may first be examined to determine that they are still functional and repaired, if possible.

Regardless of whether system 10 is provided new for each patient, if new replaceable parts are provided for each patient, or if replaceable parts are reused in multiple patients, any part of system 10 entering the subject, in particular sensor 12, and at least a segment of connector 14, such as shaft 24, may be sterilized. Theses parts may be provided to an end user pre-sterilized, or sterilized by the end user.

Monitor 16 may be operable to provide an indication of when sensor 12 detects an abnormal tissular water content. Monitor 16 may include, for example, microprocessor 50 operable to receive the signal from sensor 12 and convert the signal into a measurement of lung water content. For example, microprocessor 50 may be of the type described in U.S. Pat. No. 5,348,004, incorporated by reference herein.

Sensor 12 and monitor 16, in another embodiment, may be designed for wireless communication. In such embodiments, connector 14 and shaft 24 may be designed merely to allow removal of sensor 12 from the subject or for other functions not related to the relay of information from sensor 12 to monitor 16.

Tissular water content may be measured in any appropriate units and may be measured and expressed in more than one type of unit in the same monitor. However, in a specific embodiment it may be measured in a percentage-wise manner in relation to the tissue surrounding the sensor. In a normal human lung, the percentage should be approximately 90%.

In the embodiment of FIG. 1, an indication of lung water content may be provided through display 30. However, other methods of indication, such as noise or light, including an alarm having the methods of indication, may also be used. Display 30 may visually indicate the measured percentage or any other measurement used. Monitor 16, with or without display 30, may include an alarm that may be triggered when tissular water content varies from the expected measurement. For example, the alarm may be triggered if the tissular water content is less than approximately 89%, 88%, or 85%, or greater than approximately 91%, 92% or 95%. Monitor 16 may include a user interface to allow selection of a preferred measurement type or types, alteration of the normal value, and/or alteration of alarm parameters.

Monitor 16 may include additional components 52 operable to transmit the signal from coupler 28 to microprocessor 50 and another signal from the microprocessor to display 30 or an alarm, or both. Monitor 16 may also include a component to allow conversion of a signal from one type to another, for example from an optical signal to a digital or analog signal, and/or from a digital signal to an analog signal, or vice versa.

Monitor 16 may further be operable to perform various self-diagnostic functions. For example, it may be able to determine if its signal processing abilities are impaired, if connector 14 is properly attached and fully intact, if sensor 12 is in contact with a sufficient portion of the bronchial or tracheal wall, if connector 14 or sensor 12 is damaged, if any replaceable parts, such as a truncated portion of or all of connector 14 or sensor 12, are manufactured by the manufacturer of sensor system 10, and/or if any replaceable parts have not been changed since any previous use or have been reused and not examined for damage, sterilized, or repaired properly.

Finally, monitor 16 may include a power source and an on/off switch. Monitor 16 may include a durable outer portion to protect inner components, such as microprocessor 50.

Sensor system 10 may employ a modulated encoding scheme similar to that described in U.S. Pat. No. 6,044,283, incorporated by reference herein. It may employ a system for reducing ambient noise effects similar to that described in U.S. Pat. Nos. 5,885,213, 5,713,355, and/or 5,555,882, each incorporated by reference herein. Finally, sensor system 10 may use model-based adaptive filtering similar to that described in U.S. Pat. Nos. 6,836,679, 6,721,584, 6,411,833, 6,083,172, and/or 5,853,364, each incorporated by reference herein.

During use of a sensing system 10, a signal may be generated by the sensor. It may then travel from the sensor through connector 14 to monitor 16, where it may be used to generate an output, such as information on display 30 or an alarm.

Biocompatible material that may be used in embodiments of the present disclosure include both organic and inorganic materials, which may be used in combinations.

Figure 5:
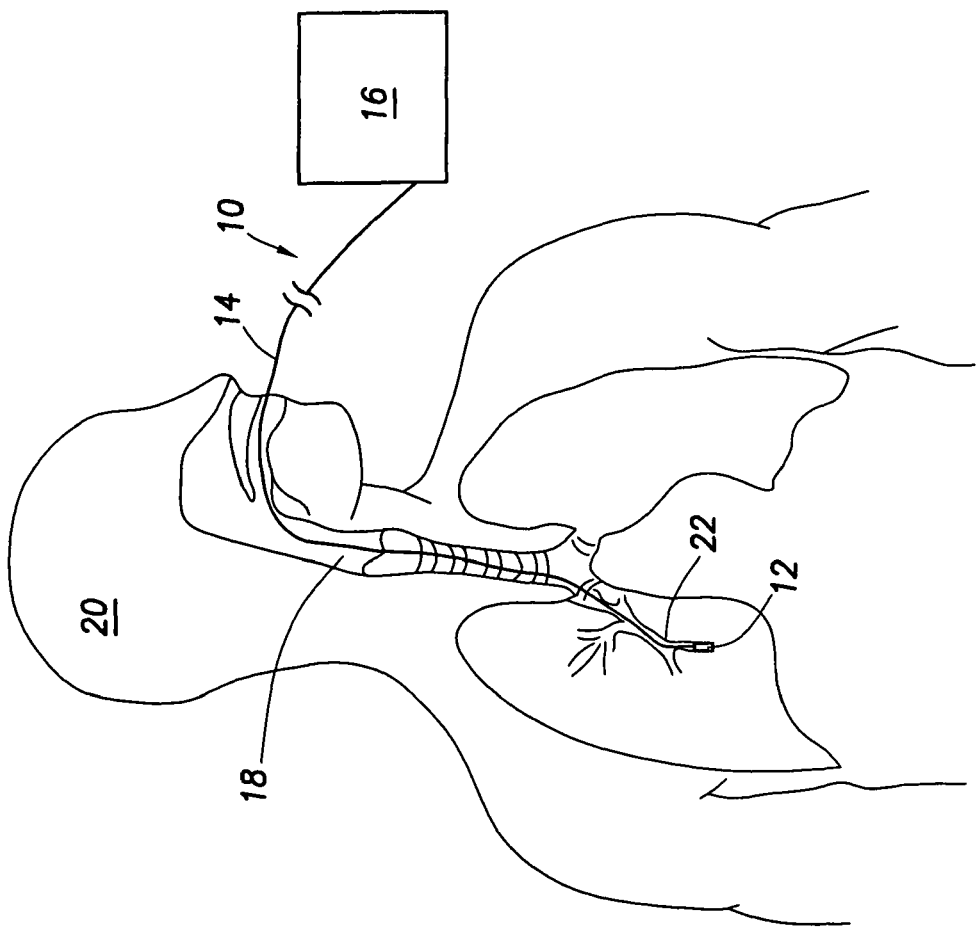
FIG. 5 is a diagram of a bronchial or tracheal sensor system in a sensing position in a human subject, according to an embodiment of the present disclosure.

When sensor system 10 is used in subject, as shown in FIG. 5, connector 14 may be inserted into airway 18 of subject 20 until sensor 12 becomes lodged against the wall of bronchus 22 (or the trachea, not shown). This process may occur as part of the process of FIG. 6. First, any replaceable part, such as sensor 12, truncated portion of connector 14, or connector 14 may be attached to the remainder of sensor system 10. Sensor 12 and adjacent portion of shaft 24 may be inserted into the airway and lowered into the lung until sensor 12 becomes lodged against bronchial wall 16 (or the tracheal wall, not shown). Tissular water content may be monitored and information about this tissular water content may be provided by monitor 16. After monitoring is completed, sensor 12 may be removed from subject 20. Truncated segment of or all of new, sterile connector 14 may be detached from coupler 32 or coupler 28, respectively, and discarded. Sensor 12 may also be detached from connector 14 and discarded.

The subject may be any animal having lungs, including an adult human, a human infant, a juvenile human, a small animal, and a large animal. In particular it may be a patient in danger of developing alveolar edema or other impairment of lung function due to excess water in the alveoli. It might also be a patient in danger of developing pulmonary dehydration. Use of sensor system 10 in any subject may facilitate therapeutic intervention in any disease or disorder the subject may have.

The sensor may be lowered into the lung blindly or it may be bronchoscopically guided. Similarly, the sensor may be removed blindly or with the aid of a bronchoscope. Although FIG. 5 illustrates insertion through the mouth, insertion may also be through the nasal passages or an artificial tracheal opening.

Monitoring may continue for any amount of time, such as approximately one hour or less, approximately one day or less, or approximately one week or less, depending upon the condition of the subject, including the measured bronchial or tracheal tissular water content. The sensor may be partially dislodged and placed in a different bronchus or portion of the tracheal or replaced with a new sensor which may also be in a different bronchus or portion of the trachea.

Although the present disclosure as illustrated by the above embodiments has been described in detail, numerous variations will be apparent to one skilled in the art. For example, a wide variety of sensors may be used. These sensors may be adapted for proper fit in a bronchus. The connector may be simpler or more complex than that depicted in the embodiments of the figures, both in terms of the number of segments which may form the connector and the portions components of these segments. The monitor may also be simpler or more complicated than that depicted in the figures. For example, the monitor may include a variety of other functions, such as the ability to measure other physiological characteristics of the subject. The monitor may even be able to integrate measurements of multiple physiological characteristics to produce information about the subject, such as a displayed measurement and/or an alarm. Additionally, the system may contain a component to allow conversion of a signal from one type to another, for example, from an optical signal to a digital or analog signal, and/or from a digital signal to an analog signal, or vice versa, other than the couplers described above. Finally, although systems methods for both the bronchia and trachea are discussed in common, not all systems and methods of the disclosure need be usable in both the bronchia and trachea. Separate bronchial and tracheal systems and methods may be provided, for example, due to different requirements to sense tissular water content in these different lung regions.

It should be understood that various changes, substitutions and alternations can be made herein without departing from the spirit and scope of the disclosure as illustrated by the following claims.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A system comprising:
   an internal spectroscopic bronchial or tracheal tissular water fraction sensor configured to be placed against bronchial or tracheal tissue and configured to generate a signal indicative of a bronchial or tracheal tissular water fraction based on a spectroscopic measurement when inserted inside a patient and placed against the bronchial or tracheal tissue;
   a connector configured to carry the signal; and
   a monitor configured to receive the signal and generate an output corresponding to the bronchial or tracheal tissular water fraction.

2. The system according to claim 1, wherein the bronchial or tracheal tissue comprises a bronchial or a tracheal wall.

3. The system according to claim 1, wherein the signal comprises an optical signal.

4. The system according to claim 1, wherein the signal comprises near infrared light.

5. The system according to claim 1, wherein the signal comprises an analog signal.

6. The system according to claim 1, wherein the signal comprises a digital signal.

7. The system according to claim 1, wherein the signal comprises an electrical signal.

8. The system according to claim 1, wherein the sensor comprises a tissue hydration probe.

9. The system according to claim 1, wherein the sensor comprises an optical fiber.

10. The system according to claim 1, wherein the sensor comprises an electrically conductive material.

11. The system according to claim 1, wherein the sensor comprises a microchip.

12. The system according to claim 1, wherein the sensor comprises a signal generator.

13. The system according to claim 1, wherein the connector comprises an optical fiber.

14. The system according to claim 1, wherein the connector comprises an electrically conductive material.

15. The system according to claim 1, wherein the connector further comprises a shaft connected to the sensor.

16. The system according to claim 15, wherein the shaft is configured to be inserted into the airway of a subject and to convey the sensor into a bronchus or the trachea of the subject.

17. The system according to claim 15, wherein the connector further comprises a cable connected to the shaft and the monitor.

18. The system according to claim 1, wherein the connector comprises at least one coupler.

19. The system according to claim 1, wherein the monitor comprises a display.

20. The system according to claim 1, wherein the monitor comprises an alarm configured to be triggered based on the output.

21. The system according to claim 1, wherein the monitor comprises a microchip.

22. The system according to claim 1, further comprising at least one component configured to convert an optical signal to a digital signal, an optical signal to an analog signal, a digital signal to an analog signal, or vice versa.

23. The system according to claim 1, further comprising at least one replaceable component.

24. The system according to claim 1, wherein the replaceable component comprises the sensor.

25. The system according to claim 1, wherein the replaceable component comprises the connector or at least a segment of the connector.

26. The system according to claim 1, wherein the monitor is configured to display the bronchial or tracheal tissular water fraction as a percentage.

27. A system comprising:
   means for sensing bronchial or tracheal tissular water percentage spectroscopically when inserted inside a patient and placed against bronchial or tracheal tissue;
   means for generating a signal indicative of the bronchial or tracheal tissular water percentage;
   means for carrying the signal; and
   means for receiving the signal and generating an output corresponding to the bronchial or tracheal tissular water percentage.

28. The system according to claim 27, wherein the bronchial or tracheal tissue comprises a bronchial or tracheal wall.

29. The system according to of claim 27, wherein the signal comprises an optical signal.

30. The system according to claim 27, wherein the signal comprises near infrared light.

31. The system according to claim 27, wherein the signal comprises an analog signal.

32. The system according to claim 27, wherein the signal comprises a digital signal.

33. The system according to claim 27, wherein the signal comprises an electrical signal.

34. A system comprising:
   an internal spectroscopic tissular water content sensor configured to be inserted inside a patient and against bronchial tissue of the patient, comprising:
      an emitter configured to emit one or more wavelengths;
      a detector configured to detect the one or more wavelengths and generate a signal in response to the detected wavelengths based on a spectroscopic measurement, wherein the signal is indicative of a content of water of the bronchial tissue; and
   a monitor configured to receive the signal from the detector, comprising:
      a microprocessor configured to determine the content of water of the bronchial tissue based on the signal and generate an output corresponding to the content of water of the bronchial tissue.

35. The system of claim 34, wherein the one or more wavelengths are sensitive to the content of water of the bronchial tissue.

36. The system of claim 34, wherein the monitor comprises an alarm triggered by the output.

* * * * *